US012721820B2

(12) United States Patent
Du et al.

(10) Patent No.: US 12,721,820 B2
(45) Date of Patent: Sep. 1, 2026

(54) METHOD OF MANUFACTURING PEPTIDE NANOPARTICLES

(71) Applicant: DuPage Medical Technology, Inc., Chicago, IL (US)

(72) Inventors: Xiaoping Du, Chicago, IL (US); Ying Liu, Clarendon Hills, IL (US)

(73) Assignee: DuPage Medical Technology, Inc., Chicago, IL (US)

( * ) Notice: Subject to any disclaimer, the term of this patent is extended or adjusted under 35 U.S.C. 154(b) by 748 days.

(21) Appl. No.: 17/802,917

(22) PCT Filed: Mar. 1, 2021

(86) PCT No.: PCT/US2021/020263
§ 371 (c)(1),
(2) Date: Aug. 26, 2022

(87) PCT Pub. No.: WO2021/174193
PCT Pub. Date: Sep. 2, 2021

(65) Prior Publication Data

US 2023/0149321 A1 May 18, 2023

Related U.S. Application Data

(60) Provisional application No. 62/983,425, filed on Feb. 28, 2020.

(51) Int. Cl.

| | |
|---|---|
| ***A61K 9/51*** | (2006.01) |
| ***A61K 9/19*** | (2006.01) |
| ***A61K 38/08*** | (2019.01) |

(52) U.S. Cl.
CPC .............. *A61K 9/5192* (2013.01); *A61K 9/19* (2013.01); *A61K 9/5123* (2013.01); *A61K 9/5146* (2013.01); *A61K 38/08* (2013.01)

(58) Field of Classification Search
CPC ......... A61K 9/5192; A61K 9/19; A61K 38/08
See application file for complete search history.

(56) References Cited

U.S. PATENT DOCUMENTS

| | | | |
|---|---|---|---|
| 8,173,595 | B2 | 5/2012 | Dai et al. |
| 8,685,921 | B2 | 4/2014 | Du |
| 9,156,884 | B2 | 10/2015 | Du |
| 10,011,634 | B2 | 7/2018 | Du |
| 10,738,080 | B2 | 8/2020 | Du |
| 12,269,900 | B2 | 4/2025 | Du |
| 2002/0115609 | A1* | 8/2002 | Onyuksel .................. A61P 9/00 514/13.1 |
| 2016/0257711 | A1 | 9/2016 | Du |
| 2022/0347113 | A1 | 11/2022 | Du et al. |

FOREIGN PATENT DOCUMENTS

| | | |
|---|---|---|
| WO | 2020056144 A1 | 3/2020 |

OTHER PUBLICATIONS

Mahato et al. Fabrication of nanostructures through molecular self-assembly of small amphiphilic glyco-dehydropeptides. Molecular Biosystems, vol. 8, 1742-1749. (Year: 2012).*
Shen et al., "A directional switch of integrin signalling and a new anti-thrombotic strategy", Nature, 503, pp. 131-135 (2013).
Liu et al., "Mixing in a multi-inlet vortex mixer (MIVM) for flash nano-precipitation", Chemical Engineering Science, 63, pp. 2829-2842 (2008).
Pang et al., "High-loading Galpha(13)-binding EXE peptide nanoparticles prevent thrombosis and protect mice from cardiac ischemia/reperfusion injury", Science Translational Medicine, 12, pp. 1-11 (2020).
Liu et al., "Micelle morphology phase diagram in a phospholipid, PEGylated lipid, and peptide amphiphiles ternary system", Chemical Engineering Research and Design, 181, pp. 354-362 (2022).
Cheng et al., "Targeting Galpha(13)-integrin interaction ameliorates systemic inflammation", Nature Communications, doi: 0.1038/s41467-021-23409-0, pp. 1-14 (2021).
Zhang et al., "Integrin beta(3) directly inhibits the Galpha(13)-p115RhoGEF interaction to regulate G protein signaling and platelet exocytosis", Nature Communications, 14:4966, pp. 1-12 (2023).
Zhang et al., "Direct Binding of Lyn to GPIbbeta Transmits 2-Way GPIb-IX Signaling to Stimulate Platelet Activation and VWF Binding", Circulation Research, 137, pp. 1480-1497 (2025).
PCT, International Search Report and Written Opinion issued in International Patent Application No. PCT/US2021/20263 on Mar. 1, 2021 (17 pages).
Mahato et al., "Fabrication of nanostructures through molecular self-assembly of small amphiphilic glyco-dehydropeptides", Molecular BioSystems, 8, pp. 1742-1749 (2012).

* cited by examiner

*Primary Examiner* — Sikarl A Witherspoon
(74) *Attorney, Agent, or Firm* — Leydig, Voit & Mayer, Ltd.

(57) ABSTRACT

Provided herein is a method of producing peptide nanoparticles comprising vortex-mixing (a) a hydrophobic or amphiphilic peptide or peptide conjugate, (b) one or more lipids that are free of a water-soluble polymer, (c) one or more lipids covalently attached to a water-soluble polymer, and (d) a hydrophilic solvent, to provide peptide nanoparticles.

19 Claims, 8 Drawing Sheets

Figure 1:
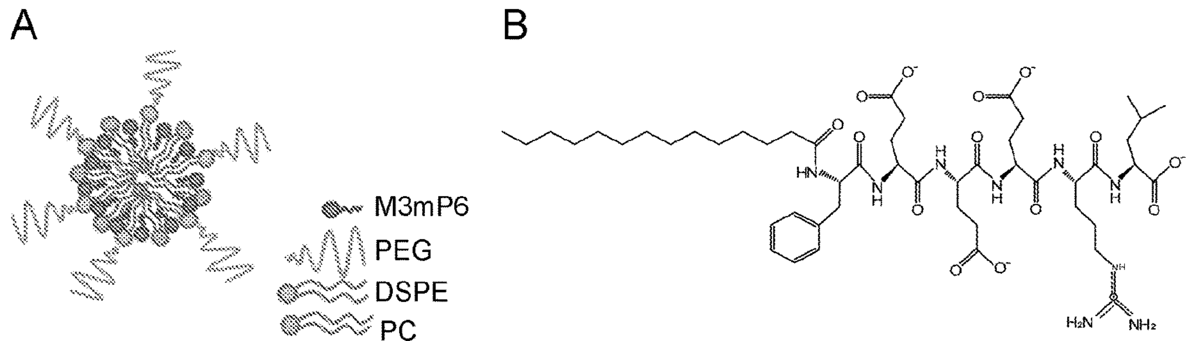

Specification includes a Sequence Listing.

A
Outlet

Micro-vortex mixer
Aqueous phase
Organic phase
(peptide and phospholipids etc)
B
Aqueous phase
Organic phase
(peptide and phospholipids etc)
Stirrer
C
Outlet
Aqueous phase
Aqueous phase
Micro-vortex mixer
Organic phase
(peptide and phospholipids etc)

(A)

(C)

METHOD OF MANUFACTURING PEPTIDE NANOPARTICLES

CROSS-REFERENCE TO RELATED APPLICATIONS

This patent application claims priority to U.S. provisional patent application 62/983,425 filed Feb. 28, 2020, the entire disclosure of which is hereby incorporated by reference.

FEDERALLY SPONSORED RESEARCH OR DEVELOPMENT

This invention was made with government support under contract HHSN268201700002C and grant 1R43HL142396, awarded by the National Institutes of Health. The government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 4 Byte ASCII (Text) file named "513396_ST25.TXT," created on Feb. 17, 2021.

BACKGROUND OF THE INVENTION

Peptides are of interest in for a variety of therapeutic, diagnostic, and research purposes. Naturally-occurring amino acid sequences or derivatives thereof that are important for biological processes (e.g., protein-protein interaction, interaction with the catalytic sites of enzymes, etc.) are particularly attractive for in vivo use as they are expected to have low toxicity and high specificity. However, efficient methods for delivering peptides into cells in vivo remain scarce, presenting a major obstacle for the development of peptide-based therapeutics and diagnostics. Although liposomes or lipid micelles can be used to deliver peptides in vivo, low concentrations of peptide incorporation into liposomes/lipid micelles make it difficult to achieve efficacious doses for clinical use, with the exception for few extremely high affinity drugs. Thus, there remains a need for improved methods of preparing compositions that can facilitate the efficient delivery of peptides in vivo.

BRIEF SUMMARY OF THE INVENTION

Provided herein is a method of producing peptide nanoparticles. In one aspect, the method comprises vortex-mixing (a) a hydrophobic or amphiphilic peptide or peptide conjugate, (b) one or more lipids that are free of a water-soluble polymer, (c) one or more lipids covalently attached to a water-soluble polymer, and (d) a hydrophilic solvent, to provide high-loading peptide nanoparticles. In another aspect, the method comprises vortex-mixing (a) an amphiphilic peptide or peptide conjugate, and (b) a hydrophilic solvent, to provide high-loading peptide nanoparticles substantially or completely without free lipid molecules. These and other aspects of the invention are provided.

BRIEF DESCRIPTION OF THE SEVERAL VIEWS OF THE DRAWING(S)

FIGS. 1A-1B shows: (A) a schematic of lipid-stabilized, high-loading peptide nanoparticles (HLPN); (B) the structure of one example of a peptide conjugated to a lipid, M3mP6 (Myr-FEEERL) peptide.

Figure 2:
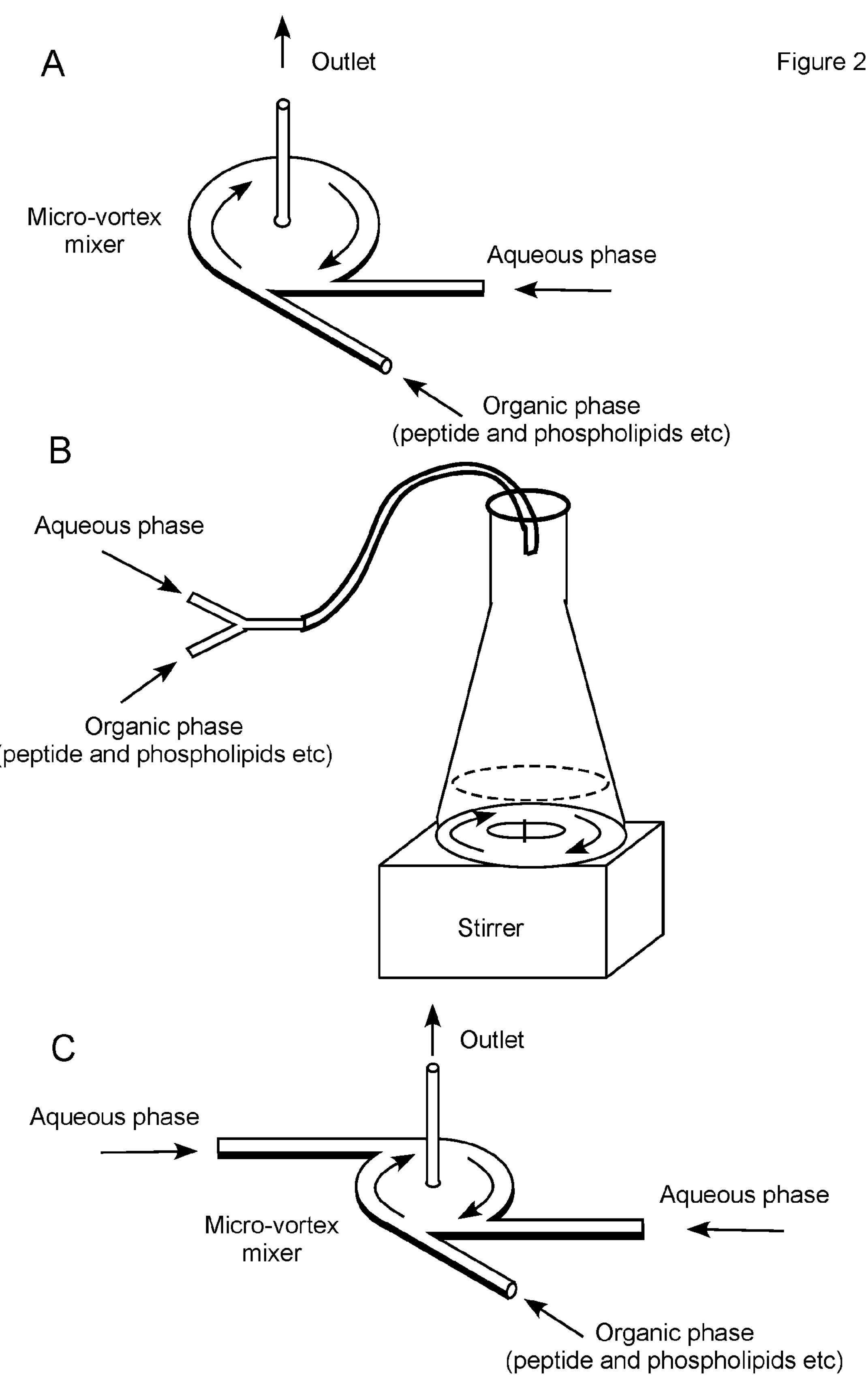

FIGS. 2A-2C shows the implementations of vortex-mixing-lyophilization technique: (A) the peptide, phospholipids and PEG-conjugated phospholipids in organic solvent (Organic phase) and an aqueous solution or solvent (aqueous phase) are pumped in a proper ratio into a micro-vortex mixer; (B) the organic phase and the aqueous phase are mixed at appropriate ratios in a flask or other container under vortex or stirring; (C) a three-way inlet vortex-mixing chamber improved from previously described multiple-inlet vortex mixer to vortex-mix the organic phase with the aqueous phase at ratios between 1:8 to 1:20.

Figure 3:
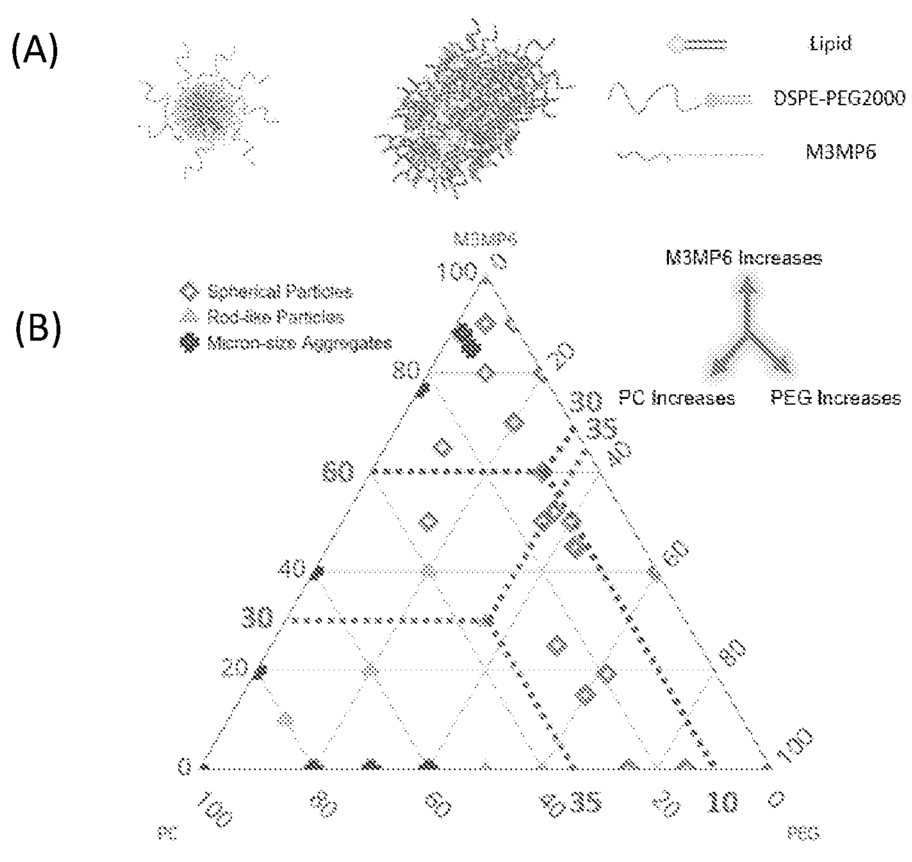
Figure 3:
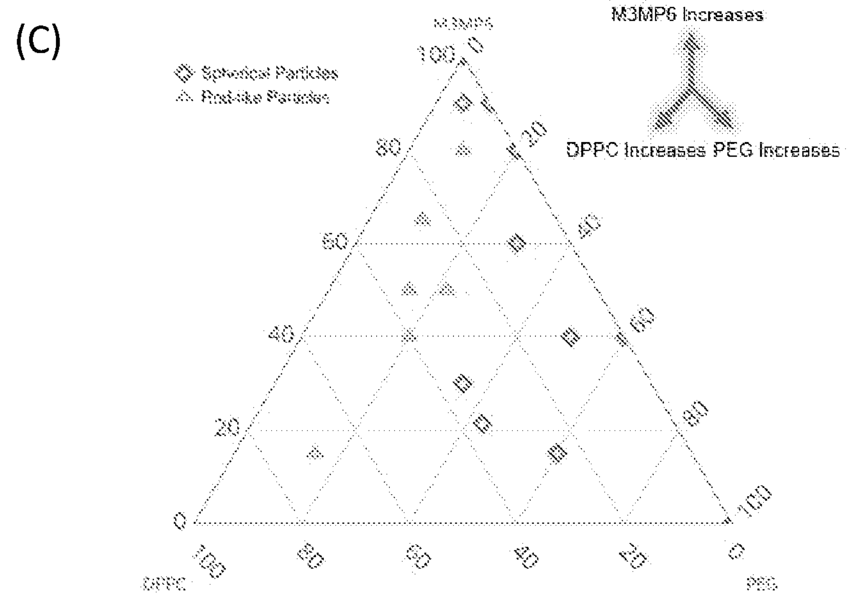

FIGS. 3A-3C provide: (A) a schematic illustration of the self-assembly structures of lipid, PEG, and M3MP6 peptide micelles: spherical and rod-like particles; (B) a ternary phase diagram of L-α-PC, PEG, and M3MP6; and (C) a ternary phase diagram of DPPC, PEG, and M3MP6.

Figure 4:
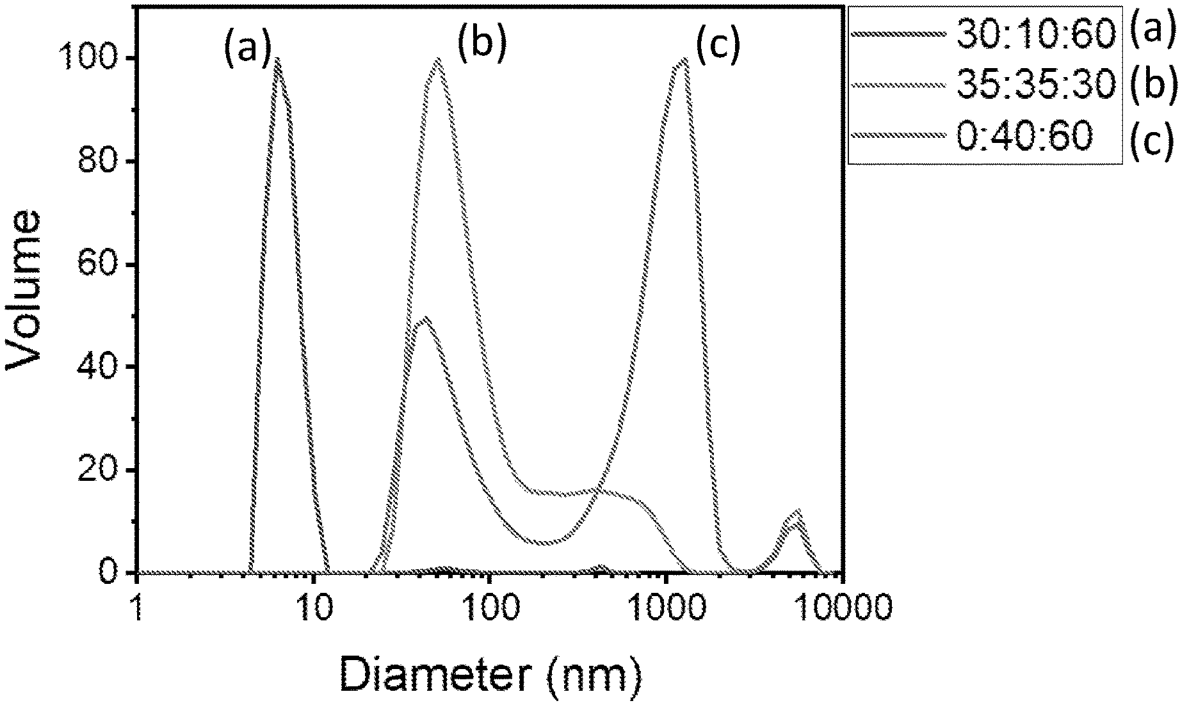
Figure 5:
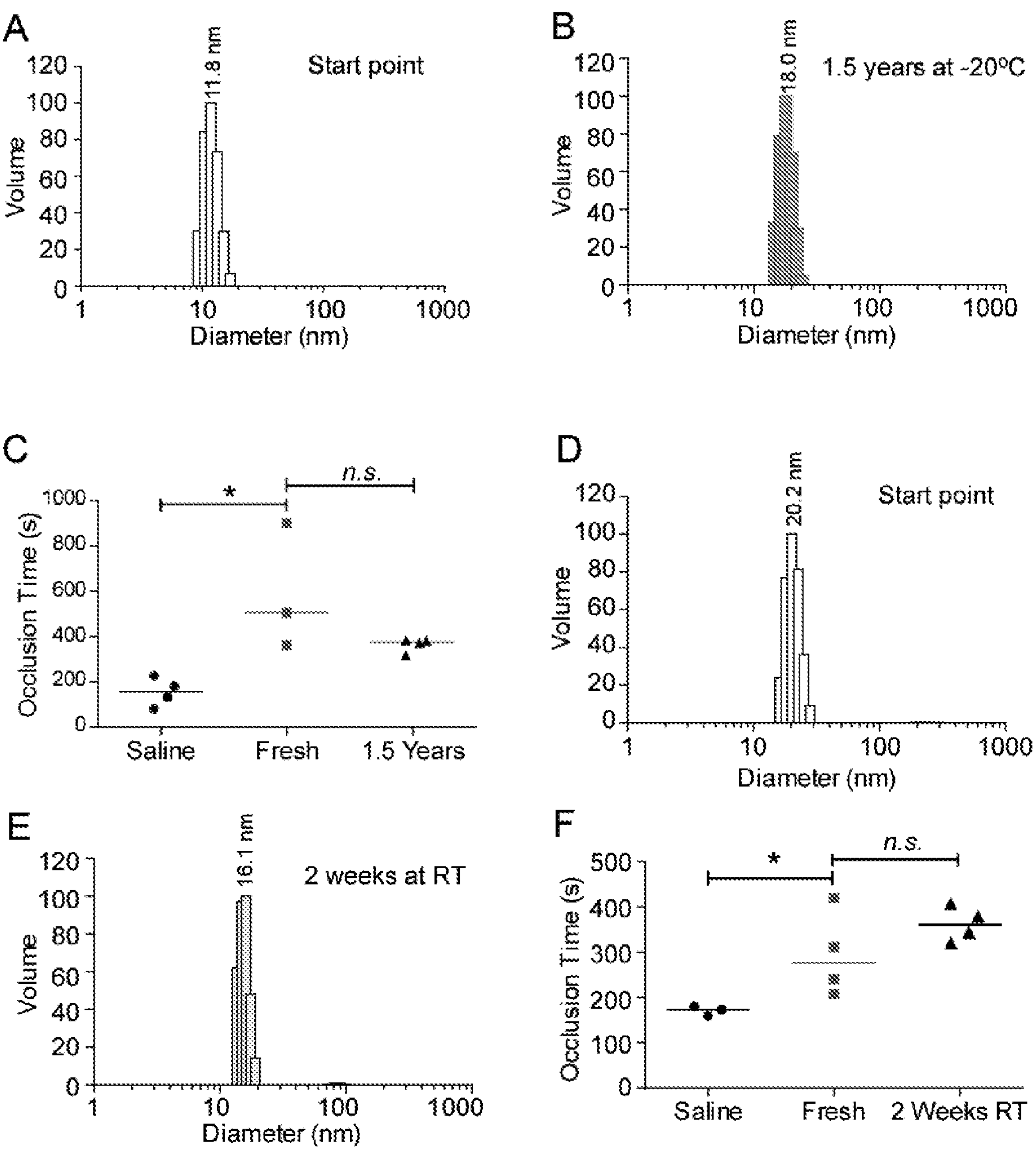

FIG. 4 provides representative DLS size measurement results for (a) spherical micelles with a molar ratio of DSPE-PEG, L-α-PC and M3MP6 30:10:60, (b) rod-like micelles with a molar ratio of DSPE-PEG, L-α-PC and M3MP6 35:35:30, and (c) micron-size aggregates with a molar ratio of DSPE-PEG, L-α-PC and M3MP6 0:40:60.

FIGS. 5A-5F shows the stability of the M3mP6 HLPN prepared using multiple inlet vortex-mixing method: (A) and (B) show Dynamic light scattering (DLS) analysis of particle sizes of M3mP6 HLPN before (A) and after (B) 18-month storage at −20° C.; (C) shows the anti-thrombotic effects of M3mP6 HLPN in $FeCl_3$-induced carotid artery thrombosis model before and after 18-month storage at −20° C. n=4, *$p<0.05$; (D and E) provide DLS-analysis of particle sizes of M3mP6 HLPN before (D) and after (E) 2-week storage at room temperature (~22° C.); (F) shows the anti-thrombotic effects of M3mP6 HLPN in $FeCl_3$-induced carotid artery thrombosis model before and after 2-week storage at room temperature. *$p<0.05$.

FIGS. 6A-6G shows that M3mP6 HLPN prepared using multiple inlet vortex-mixing method is effective in inhibiting platelet aggregation and secretion in vitro: (A) M3mP6 HLPN inhibited platelet aggregation induced by relatively low concentrations of thrombin, but not at high thrombin concentration; (B) M3mP6 HLPN inhibited both low-dose and higher-dose induced platelet secretion in human platelets; (C) M3mP6 HLPN partially inhibited collagen (1 μg/mL)-induced mouse platelet aggregation compared to scrambled peptide control. (D) M3mP6 HLPN partially inhibited U46619 (0.5 μM)-induced mouse platelet aggregation compared to scrambled peptide HLPN. (E) M3mP6 HLPN had no effects on ADP (5 μM)-induced human platelet aggregation. (F and G) M3mP6 HLPN (n=15) had no effect on protease-activated receptor agonist peptide (PAR4AP, a platelet agonist)-induced binding of JonA (an antibody indicating integrin activation) (F) and integrin ligand fibrinogen (G) to platelets.

FIGS. 7A-7D shows that the M3mP6 generated by vortex-mixing-lyophilization technique potently inhibited occlusive thrombosis without affecting bleeding, and potently inhibited both platelet thrombus formation and intravascular coagulation in vivo: (A) and (B) shows the comparison of the effects of M3mP6 HLPN, scrambled control peptide (Scra) HLPN, AAA mutant peptide (Myr-FAAARL (SEQ ID NO: 20)) HLPN and physiological saline solution on 7.5% $FeCl_3$-induced carotid artery thrombosis (A) and tail bleeding time (B) (saline: n=15, AAA: n=9, scrambled: n=6, M3mP6: n=15). ****$p<0.0001$; (C) and (D) shows M3mP6 HLPN potently inhibited platelet thrombus formation (C) and intravascular coagulation (D) in a laser-induced mouse cremaster arterial thrombosis model. In comparison, Cangrelor, a potent P2Y12 inhibitor similarly inhibited platelet thrombus formation (C) but only partially inhibited coagulation as indicated by fibrin deposition (D).

FIGS. 8A-8G shows the effects of post-ischemia injection of M3mP6 HLPN prepared using multiple inlet vortex-mixing method on myocardial ischemia and reperfusion (MI/R) injury in mice: (A) is a schematic protocol of MI/R study in which mouse left anterior descending branch (LAD) was fully ligated for 45 minutes before reopening (repurfusion); mouse chest was then closed; M3mP6 HLPN or scrambled peptide HLPN control (Scra) was bolus injected at 5 μmol/kg through jugular vein 10 minutes prior to reperfusion and then continuously infused at rate of 2.5 μmol/kg/h for 24 hours. The mice were then subject to echocardiography and/or histological examinations; (B) provides representative images of heart sections of M3mP6 HLPN- or scrambled peptide HLPN treated-mice 24 hours after reperfusion; (C) shows quantification of the infarct area (white) as percentage of the area at risk (non-blue) as shown in A; (D) shows quantification of risk area as percentage of the entire heart section, wherein viable tissue within the risk area was stained in red (n=4 for each group, $^*p<0.05$); (E) provides representative M-mode long-axis echo images for (i) sham control; (ii) MI/R treated with physiological saline; (iii) MI/R treated with platelet inhibitor cangrelor, and (iv) MI/R treated with M3mP6 HLPN; (F) shows mouse left ventricle ejection fraction detected by echocardiography and calculated by Vevo 2100 software, data was presented as mean±SEM, statistic was analyzed by one-way ANOVA using Graphpad PRISM 5.0; (G) provides Kaplan-Meier survival curve of mice 7 days after MI/R surgery treated with M3mP6 HLPN, saline control or cangrelor. Sham surgery caused no death in 6 tested mice.

DETAILED DESCRIPTION OF THE INVENTION

The method provided herein allows for the production of peptide nanoparticles. In some embodiments, the method comprises vortex-mixing (a) a hydrophobic or amphiphilic peptide or peptide conjugate, (b) one or more lipids that are free of a water-soluble polymer, (c) one or more lipids covalently attached to a water-soluble polymer, and (d) a hydrophilic solvent, to provide the high-loading peptide nanoparticles.

In some embodiments, the nanoparticles are high-loading peptide nanoparticles, which are nanoparticles comprising high levels of peptide (e.g., about 25-80 mole %, such as about 25 mole % or more, 30 mole % or more, 40 mole % or more, 50 mole % or more, 60 mole % or more, or even 70 mole % or more, based on the total nanoparticle molarity). In some embodiments, the nanoparticles comprise even higher levels of the peptide, such as about 80 mole % or more (e.g., 80-99 mole %), 90 mole % or more (e.g., about 90-99 mole %) or even about 95% or more (95-99 mole %).

In other embodiments, lower levels of peptide can be used. For instance, the peptide nanoparticles can comprise less than about 25 mole %, such as about 1-24 mole %, about 1-20 mole %, or even about 1-15 mole % or 1-10 mole % (e.g., about 5-24 mole %, about 10-24 mole %, or about 10-20 mole %).

Unless otherwise specified herein, the mole percent (mole % or percent (mol/mol)) of the components of the nanoparticle described herein are set forth with respect to the total nanoparticle molarity, meaning the total moles of molecules constituting the components of the nanoparticle (e.g., total moles of the (a) a hydrophobic or amphiphilic peptide or peptide conjugate, (b) one or more lipids that are free of a water-soluble polymer, and (c) one or more lipids covalently attached to a water-soluble polymer) but not including solvent or water molecules.

Without wishing to be bound by any particular theory or mechanism of action, it is believed that combining the (a) a hydrophobic or amphiphilic peptide or peptide conjugate, (b) one or more lipids that are free of a water-soluble polymer, (c) one or more lipids covalently attached to a water-soluble polymer, and (d) a hydrophilic solvent, by vortex mixing as described herein allows formation of lipid-stabilized peptide nanoparticle, in which high-loading levels of the peptide are facilitated within the walls of the nanoparticle rather than only in the core of the nanoparticle. It is believed, again without wishing to be bound by any such theory or mechanism of action, that the peptide-based nanoparticle with a relatively small amount of lipids free of a water-soluble polymer and lipids attached to a water-soluble polymer in the walls of the nanoparticle prevents the clustering and formation of large precipitates or gel, and facilitates the efficient delivery of the peptide to intracellular targets in vitro and in vivo. The vortex mixing of (a) a hydrophobic or amphiphilic peptide or peptide conjugate, (b) one or more lipids that are free of a water-soluble polymer, (c) one or more lipids covalently attached to a water-soluble polymer, and (d) a hydrophilic solvent, can be facilitated by any method that creates a vortex (e.g., any method that creates a region in a fluid in which the flow revolves around an axis line) (see, e.g., FIGS. 2A-2C). Suitable vortex mixers are known in the art and include, for example, stirrers or impeller mixers, blade-type and other high shear mixers, confined impinging jet (CIJ) mixers (e.g., Han et al, J Pharm Sci., 101 (10) 40180-4023 (2012)), and multi-inlet vortex mixers (MIVM) (e.g., Y. Liu, Cheng, Y., Liu, Y., Prud'homme, R. K., Fox, R. O., "Mixing in a multi-inlet vortex mixer (MIVM) for flash nano-precipitation." Chemical Engineering Science 63, 2829-2842 (2008); Markwalter et al., J Pharm Sci. 107(9): 2465-2471 (2018)). In an embodiment, an MIVM mixer is used.

In one aspect of the method, the (a) a hydrophobic or amphiphilic peptide or peptide conjugate, (b) one or more lipids that are free of a water-soluble polymer, and (c) one or more lipids covalently attached to a water-soluble polymer, are combined with an organic solvent to provide an organic phase, and the organic phase is combined by vortex mixing with a hydrophilic solvent that provides an aqueous phase. By way of further illustration, the organic phase can be provided as a first stream and the aqueous phase can be provided as a second stream, and the streams can be combined under flow conditions sufficient to create a vortex (e.g., turbulent flow conditions). The conditions that create the vortex can be any of various means known in the art, such as a mechanical stirring or mixing apparatus, a passage way designed to create a vortex in the converging or impinging streams, or otherwise by virtue of the velocity of the streams and/or the angle of the streams relative to one another or to the structure of the mixer as they are combined. For example, the organic phase and aqueous phase can be vortex-mixed by pumping them through a multi-inlet vortex mixing apparatus or micro-vortex mixing apparatus. Examples of such apparatus are demonstrated in the drawings of FIGS. 2A-2C and disclosed in the art (e.g., Markwalter et al., J Pharm Sci. 107(9): 2465-2471 (2018); Shen, H., et al., "Enhanced oral bioavailability of a cancer preventive agent (SR13668) by employing polymeric nanoparticles with high drug loading." J Pharm Sci 101, 3877-3885 (2012).

The organic solvent used will depend upon the particular peptide or peptide conjugate, lipids free of a water-soluble polymer, and lipids attached to a water soluble polymer that are used. Any solvent capable of solubilizing the peptides and lipids is suitable. When the nanoparticle is for use as a pharmaceutical agent in humans and animals, the solvent should be safe for use in humans or animals, or should be capable of being substantially or completely removed (i.e., reduced to levels safe for use in humans or animals) prior to use. Examples of suitable organic solvents include alcohols (e.g., methanol, ethanol, or a mixture thereof), ethers, ketones, aldehydes, chloroform, acetonitrile, carboxylic acids (e.g., formic acid or acetic acid), or various hydrocarbons. In some embodiments, the organic solvent is miscible with water. In some embodiments, the solvent is an alcohol. In particular embodiments, the solvent is ethanol, methanol, or a mixture thereof.

The hydrophilic solvent can be any solvent that forms a separate phase (e.g., a hydrophilic phase or an aqueous phase) when combined with the organic solvent that provides an organic phase. In some embodiments, the hydrophilic solvent is an aqueous solvent or water. Other examples of hydrophilic solvents include aqueous solutions including buffered solutions preferably at physiological concentrations (e.g., aqueous saline, such as 0.15 N NaCl; phosphate-buffered saline, and the like).

The method can be used with respect to any hydrophobic or amphiphilic peptide or peptide conjugate. The peptide or peptide conjugate can comprise any suitable number of amino acid residues. In some embodiments, the hydrophobic or amphiphilic peptide or peptide conjugate comprises 2 or more amino acid residues (e.g., about 3 or more, about 4 or more, or about 5 or more amino acid residues) and about 50 or fewer amino acid residues (e.g., about 40 or fewer, about 30 or fewer, about 20 or fewer or about 10 or fewer amino acid residues). Any of foregoing approximate upper and lower limits can be expressed as a range (e.g., about 2-50, about 2-40, about 2-30, about 2-20, about 2-15, about 2-10, about 4-40, about 4-30, about 4-20, about 4-15, or about 4-10 amino acid residues). The choice of a particular peptide for use in conjunction with the claimed method will depend upon the desired end use, e.g., the desired therapeutic application. Examples of peptides include, for instance, FEEERI (SEQ ID NO: 1), FEKEKI (SEQ ID NO: 2), FEKERI (SEQ ID NO: 3), RGT (SEQ ID NO: 4), EEERA (SEQ ID NO: 5), FEEERA (SEQ ID NO: 6), FEEERM (SEQ ID NO: 7), FEEERL (SEQ ID NO: 8), FEKEKM (SEQ ID NO: 9), FEKEKL (SEQ ID NO: 10), FEKERM (SEQ ID NO: 11), FEKERL (SEQ ID NO: 12), CFEEERAC (SEQ ID NO: 13), FEEERAR (SEQ ID NO: 14), FEEERARA (SEQ ID NO: 15), SIRYSGHpSL (SEQ ID NO: 16), KFEEERARAKWDT (SEQ ID NO: 17), and the like. Other peptides can also be formulated as HLPN for delivery into cells, such as RCLLPA (SEQ ID NO: 18) (Rusu et al, Blood 123(3):442-50, 2014), and LLARRPTKGIHEY (SEQ ID NO: 19) (Huang J-S et al, JBC 282, 10210-10222, 2007).

In some embodiments, the peptide may be cyclized. For example, the peptide may comprise two Cys residues, the sulfur atoms of which participate in the formation of a disulfide bridge. In exemplary aspects, the peptide comprises a Cys residue as the terminal residues. In a particular embodiment, the peptide is CFEEERAC (SEQ ID NO: 13). Suitable methods of modifying peptides with disulfide bridges or sulfur-based cyclization are described in, for example, Jackson et al., *J. Am. Chem. Soc.* 113: 9391-9392 (1991) and Rudinger and Jost, Experientia 20: 570-571 (1964). Other means of peptide cyclizing are reviewed in Davies, J. Peptide. Sci. 9: 471-501 (2003). Such means include the formation of an amide bridge, thioether bridge, thioester bridge, urea bridge, carbamate bridge, sulfonamide bridge, and the like. For example, a thioester bridge can be formed between the C-terminus and the side chain of a Cys residue. Alternatively, a thioester can be formed via side chains of amino acids having a thiol (Cys) and a carboxylic acid (e.g., Asp, Glu). In another method, a cross-linking agent, such as a dicarboxylic acid, e.g., suberic acid (octanedioic acid), etc. can introduce a link between two functional groups of an amino acid side chain, such as a free amino, hydroxyl, thiol group, and combinations thereof.

Such peptides may be obtained by methods known in the art, and the peptides can be synthetic, recombinant, isolated, and/or purified. Suitable methods of producing peptides are described in, for example, Chan et al., Fmoc Solid Phase Peptide Synthesis, Oxford University Press, Oxford, United Kingdom, 2005; Peptide and Protein Drug Analysis, ed. Reid, R., Marcel Dekker, Inc., 2000; Epitope Mapping, ed. Westwood et al., Oxford University Press, Oxford, United Kingdom, 2000; and U.S. Pat. No. 5,449,752; Sambrook et al., Molecular Cloning: A Laboratory Manual. 3rd ed., Cold Spring Harbor Press, Cold Spring Harbor, N.Y. 2001; and Ausubel et al., Current Protocols in Molecular Biology, Greene Publishing Associates and John Wiley & Sons, N Y, 1994.

In some embodiments, the peptide itself is hydrophobic or amphiphilic and is not necessarily conjugated to any other moiety (although a hydrophobic or amphiphilic peptide can be conjugated to another hydrophilic or hydrophobic moiety provided the resulting conjugate is hydrophilic or amphiphilic). In other embodiments, the peptide (e.g., a hydrophilic peptide) is conjugated to a hydrophobic moiety to provide a hydrophobic or amphiphilic peptide conjugate.

The peptide can be conjugated to any suitable hydrophobic groups. For instance, the the peptide can be conjugated to a second, hydrophobic or amphiphilic peptide, such as a peptide comprising a transmembrane domain (e.g., IL2 receptor alpha transmembrane domain), or to a phospholipid (e.g., DSPE) or hydrophobic polymer. In other embodiments, the peptide is conjugated to an alkyl, acyl, or aryl group comprising any suitable number of carbon atoms (e.g., 6-20 carbon atoms or 10-20 carbon atoms). In some embodiments, the peptide is conjugated with a fatty acid, such as caprylic acid (C8), capric acid (C10), lauric acid (C12), myristic acid (C14), palmitic acid (C16) and stearic acid (C18), providing a peptide conjugate with the corresponding lipid group (e.g., capryloyl, caproyl, lauroyl, myristoyl, palmitoyl, or stearoyl group). Also, cysteine groups in the peptide can be can be palmitoylated. In particular embodiments, the peptide is myristylated, stearylated or palmitoylated at the N terminal amino acid. In an embodiment, the peptide is myristylated at the N-terminal amino acid. In other embodiments, the peptide is palmitoylated at the N terminal amino acid.

Specific examples of conjugated peptides include myr-FEEERI (SEQ ID NO: 1), myr-FEKEKI (SEQ ID NO: 2), myr-FEKERI (SEQ ID NO: 3), myr-RGT (SEQ ID NO: 4), myr-EEERA (SEQ ID NO: 5), myr-FEEERA (SEQ ID NO: 6), myr-FEEERM (SEQ ID NO: 7), myr-FEEERL (SEQ ID NO: 8), myr-FEKEKM (SEQ ID NO: 9), myr-FEKEKL (SEQ ID NO: 10), myr-FEKERM (SEQ ID NO: 11), myr-FEKERL (SEQ ID NO: 12), myr-CFEEERAC (SEQ ID NO: 13), myr-FEEERAR (SEQ ID NO: 14), myr-FEEERARA (SEQ ID NO: 15), myr-SIRYSGHpSL (SEQ ID NO: 16), myr-KFEEERARAKWDT (SEQ ID NO: 17), myr-RCLLPA (SEQ ID NO: 18), and myr-LLARRPTKGIHEY (SEQ ID NO: 19). In particular embodiments, the lipid stabilized peptide is myr-FEEERL (SEQ ID NO: 8) or myr-FEKEKL (SEQ ID NO: 10). Those of ordinary skill in the art will appreciate that the myristoyl group (myr-) in any of the foregoing can be replaced with any other suitable fatty acid group, such as those mentioned above (e.g., a palmitoyl group).

Regardless of whether the peptide is conjugated to a hydrophobic moiety or not, the peptide can comprise one or more other modifications including, without limitation phosphorylation, glycosylation, hydroxylation, sulfonation, amidation, acetylation, carboxylation, introduction of non-hydrolyzable bonds, disulfide formation and conjugation or linking to a targeting or carrier peptide. In some embodiments, the modification may improve the stability and/or activity of the peptides in storage or in use (e.g., in vivo). For example, the C-terminal may be modified with amidation, addition of peptide alcohols and aldehydes, addition of esters, addition of p-nitorailine and thioesters and multiple antigens peptides. The N-terminal and side chains may be modified by PEGylation, acetylation, formylation, addition of a fatty acid, addition of benzoyl, addition of bromoacetyl, addition of pyroglutamyl, succinylation, addition of tetrabutyoxycarbonyl and addition of 3-mercaptopropyl, acylations, biotinylation, phosphorylation, sulfation, glycosylation, introduction of maleimido group, chelating moieties, chromophores and fluorophores. In some embodiments, the peptide is attached or linked or conjugated to a second moiety (e.g., a heterologous moiety, a conjugate moiety). The heterologous moiety any molecule (chemical or biochemical, naturally-occurring or synthetic) which is different from the peptide. Exemplary heterologous moieties include, but are not limited to, a polymer, a carbohydrate, a lipid, a nucleic acid, an oligonucleotide, a DNA or RNA, an amino acid, peptide, polypeptide, protein, therapeutic agent, (e.g., a cytotoxic agent, cytokine), or a diagnostic agent.

For example, the C-terminal may be modified with amidation, addition of peptide alcohols and aldehydes, addition of esters, addition of p-nitorailine and thioesters and multipelantigens peptides. The N-terminal and side chains may be modified by PEGylation, acetylation, formylation, addition of a fatty acid, addition of benzoyl, addition of bromoacetyl, addition of pyroglutamyl, succinylation, addition of tetrabutyoxycarbonyl and addition of 3-mercaptopropyl, acylations (e.g. lipopeptides), biotinylation, phosphorylation, sulfation, glycosylation, introduction of maleimido group, chelating moieties, chromophores and fluorophores.

The one or more lipids free of a water soluble polymer can comprise any lipid suitable for use in preparing micelles and liposomes used for encapsulating compounds and peptides for drug delivery. Such peptides are known in the art, non-limiting examples of which include phosphatidylcholine (PC), phosphatidylglycerol (PG), phosphatidylethanolamine (PE), phosphatidyl-serine (PS), phosphatidyl-inositol (PI), mixtures thereof, and the like. See, e.g., Banerjee and Onyuksel, Peptide Delivery Using Phospholipid Micelles, WIREs Nanomed Nanobiotechnol 4:562-574 (2012). In a particular embodiment, the lipid free of a water soluble polymer is phosphatidylcholine.

Similarly, the one or more lipids attached to a water soluble polymer can comprise any lipid suitable for use in preparing micelles and liposomes used for encapsulating compounds and peptides for drug delivery. By "attached," it is meant that the lipid is covalently bound to the water soluble polymer. Representative lipids attached to a water soluble polymer include a fatty acid or mixture of fatty acids conjugated to PEG (poly(ethylene glycol)-PE, PEG-PC, PEG-PG, PEG-PI, PEG-PS, PEG-DSPE, and the like. In some embodiments, the PEG attached to the lipid has a molecular weight of about 400-50,000 or higher (e.g., about 400-10,000, about 1000-5000, or about 1000-3000). In a particular embodiment, the lipid covalently attached to a water soluble polymer is 1,2-distearoyl-sn-glycero-3-phosphoethanolamine-N-[amino(polyethylene glycol)-2000].

The (a) a hydrophobic or amphiphilic peptide or peptide conjugate, (b) one or more lipids that are free of a water-soluble polymer, and (c) one or more lipids covalently attached to a water-soluble polymer can be combined in any suitable proportion to provide the peptide nanoparticle with the desired loading level. The ratio of these different components can be adjusted to affect the shapes, sizes and other properties of the nanoparticles (see, e.g., FIGS. 3A-3C). In an illustrative embodiment, the lipid-stabilized, high-loading peptide nanoparticle (e.g., comprising about 25 mole % or more or 30 mole % or more of the peptide, such as about 30-80 mole % or 36-80 mole % of the peptide) comprises about 2-20 mole % (e.g., about 2-10%) of one or more lipids free of a water soluble polymer (e.g., phosphatidylcholine) and about 10-60 mole % lipid attached to a water soluble polymer (e.g., PEG-DSPE).

The components can be combined by providing the amphiphilic or hydrophobic peptide, one or more lipids free of a water soluble polymer, one or more lipids covalently attached to a water-soluble polymer, and organic solvent (e.g., in the forgoing proportions) as an organic phase, and combining (e.g., by vortex mixing) with an aqueous phase comprising a hydrophilic solvent, wherein the volume ratio of the organic phase to the aqueous phase is between about 1:5 and 1:50 (e.g., about 1:5 to 1:40 or about 1:8 to 1:20). By way of illustration, a lipid-stabilized high loading peptide nanoparticle (e.g., comprising a lipidated peptide, such as M3mP6 used in the examples) can be made by providing an organic phase comprising about 30-80% (mol/mol) (e.g., about 60% (mol/mol) of the hydrophobic or amphiphilic peptide, about 2-20% (mol/mol) (e.g., about 10% (mol/mol) of one or more lipids free of a water soluble polymer (e.g., phosphatidylcholine), and about 10-60% (mol/mole) (e.g., about 30% (mol/mol)) of one or more lipid attached to a water soluble polymer (e.g., DSPE-PEG2000) dissolved in an organic solvent (e.g., an alcohol such as methanol or ethanol) and vortex-mixing the organic phase with an aqueous phase (e.g., water) at about 5 to 50 (e.g., about 5 to 40) times the volume of the organic phase (e.g., 8 to 20 times the volume, or about 12 times the volume of the organic phase). Mole percent (mol/mol) of the nanoparticle components of the organic phase, as referenced above, is the number of moles of the listed component as a percentage of the total number of moles of all components of the nanoparticle (e.g., lipidated or amphiphilic peptide, lipid free of a water soluble polymer, and lipid attached to a water soluble polymer) excluding solvent or water molecules.

Another aspect of the disclosure provides a method of producing peptide nanoparticles as described herein comprising vortex-mixing (a) an organic phase comprising a hydrophobic or amphiphilic peptide or peptide conjugate and one of (i) one or more lipids that are free of a water-soluble polymer, or (ii) one or more lipids covalently attached to a water-soluble polymer, and (d) a hydrophilic solvent, to provide lipid-stabilized high-loading peptide nanoparticles. Thus, according to this method, only one of the two types of lipids are required. All other aspects of the method are as previously described.

Another aspect of the disclosure provides a method of preparing a peptide nanoparticle by vortex-mixing (a) an amphiphilic peptide solubilized in organic phase with (b) a hydrophilic solvent (aqueous phase), wherein the peptide nanoparticle is substantially or completely without lipids other than, optionally, a lipid that may be attached to the amphiphilic peptide. All other aspects of the method are as previously described. Thus, for instance, vortex mixing can be facilitated by any method that creates a vortex (e.g., any method that creates a region in a fluid in which the flow revolves around an axis line) (see, e.g., FIGS. 2A-2C). Suitable vortex mixers are known in the art and include, for example, stirrers or impeller mixers, blade-type and other high shear mixers, confined impinging jet (CIJ) mixers (e.g., Han et al, J Pharm Sci., 101 (10) 40180-4023 (2012)), and multi-inlet vortex mixers (MIVM) (e.g., Y. Liu, Cheng, Y., Liu, Y., Prud'homme, R. K., Fox, R. O., "Mixing in a multi-inlet vortex mixer (MIVM) for flash nano-precipitation." Chemical Engineering Science 63, 2829-2842 (2008); Markwalter et al., J Pharm Sci. 107(9): 2465-2471 (2018)). In an embodiment, an MIVM mixer is used.

The amphiphilic peptide or peptide conjugate combined with an organic solvent to provide an organic phase is combined by vortex mixing with a hydrophilic solvent that provides an aqueous phase. By way of further illustration, the organic phase can be provided as a first stream and the aqueous phase can be provided as a second stream, and the streams can be combined under flow conditions sufficient to create a vortex (e.g., turbulent flow conditions). The conditions that create the vortex can be any of various means known in the art, such as a mechanical stirring or mixing apparatus, a passage way designed to create a vortex in the converging or impinging streams, or otherwise by virtue of the velocity of the streams and/or the angle of the streams relative to one another or to the structure of the mixer as they are combined. For example, the organic phase and aqueous phase can be vortex-mixed by pumping them through a multi-inlet vortex mixing apparatus or micro-vortex mixing apparatus. Examples of such apparatus are demonstrated in the drawings of FIGS. 2A-2C and disclosed in the art (e.g., Markwalter et al., J Pharm Sci. 107(9): 2465-2471 (2018); Shen, H., et al., "Enhanced oral bioavailability of a cancer preventive agent (SR13668) by employing polymeric nanoparticles with high drug loading." J Pharm Sci 101, 3877-3885 (2012).

The organic solvent used will depend upon the particular amphiphilic peptide or peptide conjugate. Any solvent capable of solubilizing the amphiphilic peptide or peptide conjugate is suitable. When the nanoparticle is for use as a pharmaceutical agent in humans and animals, the solvent should be safe for use in humans or animals, or should be capable of being substantially or completely removed (i.e., reduced to levels safe for use in humans or animals) prior to use. Examples of suitable organic solvents include alcohols (e.g., methanol, ethanol, or a mixture thereof), ethers, ketones, aldehydes, chloroform, acetonitrile, carboxylic acids (e.g., formic acid or acetic acid), or various hydrocarbons. In some embodiments, the organic solvent is miscible with water. In some embodiments, the solvent is an alcohol. In particular embodiments, the solvent is ethanol, methanol, or a mixture thereof.

The hydrophilic solvent can be any solvent that forms a separate phase (e.g., a hydrophilic phase or an aqueous phase) when combined with the organic solvent that provides an organic phase. In some embodiments, the hydrophilic solvent is an aqueous solvent or water. Other examples of hydrophilic solvents include aqueous solutions including buffered solutions preferably at physiological concentrations (e.g., aqueous saline, such as 0.15 N NaCl; phosphate-buffered saline, and the like).

The method can be used with respect to any amphiphilic peptide or peptide conjugate. The peptide or peptide conjugate can comprise any suitable number of amino acid residues. In some embodiments, the hydrophobic or amphiphilic peptide or peptide conjugate comprises 2 or more amino acid residues (e.g., about 3 or more, about 4 or more, or about 5 or more amino acid residues) and about 50 or fewer amino acid residues (e.g., about 40 or fewer, about 30 or fewer, about 20 or fewer or about 10 or fewer amino acid residues). Any of foregoing approximate upper and lower limits can be expressed as a range (e.g., about 2-50, about 2-40, about 2-30, about 2-20, about 2-15, about 2-10, about 4-40, about 4-30, about 4-20, about 4-15, or about 4-10 amino acid residues). The choice of a particular peptide for use in conjunction with the claimed method will depend upon the desired end use, e.g., the desired therapeutic application. Examples of peptides include, for instance, FEEERI (SEQ ID NO: 1), FEKEKI (SEQ ID NO: 2), FEKERI (SEQ ID NO: 3), RGT (SEQ ID NO: 4), EEERA (SEQ ID NO: 5), FEEERA (SEQ ID NO: 6), FEEERM (SEQ ID NO: 7), FEEERL (SEQ ID NO: 8), FEKEKM (SEQ ID NO: 9), FEKEKL (SEQ ID NO: 10), FEKERM (SEQ ID NO: 11), FEKERL (SEQ ID NO: 12), CFEEERAC (SEQ ID NO: 13), FEEERAR (SEQ ID NO: 14), FEEERARA (SEQ ID NO: 15), SIRYSGHpSL (SEQ ID NO: 16), KFEEERARAKWDT (SEQ ID NO: 17), and the like. Other peptides can also be formulated as HLPN for delivery into cells, such as RCLLPA (SEQ ID NO: 18) (Rusu et al, Blood 123(3):442-50, 2014), and LLARRPTKGIHEY (SEQ ID NO: 19) (Huang J-S et al, JBC 282, 10210-10222, 2007).

In some embodiments, the peptide may be cyclized. For example, the peptide may comprise two Cys residues, the sulfur atoms of which participate in the formation of a disulfide bridge. In exemplary aspects, the peptide comprises a Cys residue as the terminal residues. In a particular embodiment, the peptide is CFEEERAC (SEQ ID NO: 13). Suitable methods of modifying peptides with disulfide bridges or sulfur-based cyclization are described in, for example, Jackson et al., *J. Am. Chem. Soc.* 113: 9391-9392 (1991) and Rudinger and Jost, Experientia 20: 570-571 (1964). Other means of peptide cyclizing are reviewed in Davies, J. Peptide. Sci. 9: 471-501 (2003). Such means include the formation of an amide bridge, thioether bridge, thioester bridge, urea bridge, carbamate bridge, sulfonamide bridge, and the like. For example, a thioester bridge can be formed between the C-terminus and the side chain of a Cys residue. Alternatively, a thioester can be formed via side chains of amino acids having a thiol (Cys) and a carboxylic acid (e.g., Asp, Glu). In another method, a cross-linking agent, such as a dicarboxylic acid, e.g., suberic acid (octanedioic acid), etc. can introduce a link between two functional groups of an amino acid side chain, such as a free amino, hydroxyl, thiol group, and combinations thereof.

Such peptides may be obtained by methods known in the art, and the peptides can be synthetic, recombinant, isolated, and/or purified. Suitable methods of producing peptides are described in, for example, Chan et al., Fmoc Solid Phase Peptide Synthesis, Oxford University Press, Oxford, United Kingdom, 2005; Peptide and Protein Drug Analysis, ed. Reid, R., Marcel Dekker, Inc., 2000; Epitope Mapping, ed. Westwood et al., Oxford University Press, Oxford, United Kingdom, 2000; and U.S. Pat. No. 5,449,752; Sambrook et al., Molecular Cloning: A Laboratory Manual. 3rd ed., Cold Spring Harbor Press, Cold Spring Harbor, N.Y. 2001; and Ausubel et al., Current Protocols in Molecular Biology, Greene Publishing Associates and John Wiley & Sons, N Y, 1994.

In some embodiments, the peptide itself is amphiphilic and is not necessarily conjugated to any other moiety (although an amphiphilic peptide can be conjugated to another hydrophilic or hydrophobic moiety provided the resulting conjugate is hydrophilic or amphiphilic). In other embodiments, the peptide (e.g., a hydrophilic peptide) is conjugated to a hydrophobic moiety to provide a hydrophobic or amphiphilic peptide conjugate.

The peptide can be conjugated to any suitable hydrophobic groups. For instance, the the peptide can be conjugated to a second hydrophobic or amphiphilic peptide, such as a peptide comprising a transmembrane domain (e.g., IL2 receptor alpha transmembrane domain), or to a phospholipid (e.g., DSPE) or hydrophobic polymer. In other embodiments, the peptide is conjugated to an alkyl, acyl, or aryl group comprising any suitable number of carbon atoms (e.g., 6-20 carbon atoms or 10-20 carbon atoms). In some embodiments, the peptide is conjugated with a fatty acid, such as caprylic acid (C8), capric acid (C10), lauric acid (C12), myristic acid (C14), palmitic acid (C16) and stearic acid (C18), providing a peptide conjugate with the corresponding lipid group (e.g., capryloyl, caproyl, lauroyl, myristoyl, palmitoyl, or stearoyl group). Also, cysteine groups in the peptide can be can be palmitoylated. In particular embodiments, the peptide is myristylated, stearylated or palmitoylated at the N terminal amino acid. In an embodiment, the peptide is myristylated at the N-terminal amino acid. In other embodiments, the peptide is palmitoylated at the N terminal amino acid.

Specific examples of conjugated peptides include myr-FEEERI (SEQ ID NO: 1), myr-FEKEKI (SEQ ID NO: 2), myr-FEKERI (SEQ ID NO: 3), myr-RGT (SEQ ID NO: 4), myr-EEERA (SEQ ID NO: 5), myr-FEEERA (SEQ ID NO: 6), myr-FEEERM (SEQ ID NO: 7), myr-FEEERL (SEQ ID NO: 8), myr-FEKEKM (SEQ ID NO: 9), myr-FEKEKL (SEQ ID NO: 10), myr-FEKERM (SEQ ID NO: 11), myr-FEKERL (SEQ ID NO: 12), myr-CFEEERAC (SEQ ID NO: 13), myr-FEEERAR (SEQ ID NO: 14), myr-FEEERARA (SEQ ID NO: 15), myr-SIRYSGHpSL (SEQ ID NO: 16), myr-KFEEERARAKWDT (SEQ ID NO: 17), myr-RCLLPA (SEQ ID NO: 18), and myr-LLARRPTKGIHEY (SEQ ID NO: 19). In particular embodiments, the lipid stabilized peptide is myr-FEEERL (SEQ ID NO: 8) or myr-FEKEKL (SEQ ID NO: 10). Those of ordinary skill in the art will appreciate that the myristoyl group (myr-) in any of the foregoing can be replaced with any other suitable fatty acid group, such as those mentioned above (e.g., a palmitoyl group).

Regardless of whether the peptide is conjugated to a hydrophobic moiety or not, the peptide can comprise one or more other modifications including, without limitation phosphorylation, glycosylation, hydroxylation, sulfonation, amidation, acetylation, carboxylation, introduction of non-hydrolyzable bonds, disulfide formation and conjugation or linking to a targeting or carrier peptide. In some embodiments, the modification may improve the stability and/or activity of the peptides in storage or in use (e.g., in vivo). For example, the C-terminal may be modified with amidation, addition of peptide alcohols and aldehydes, addition of esters, addition of p-nitoraline and thioesters and multiple antigens peptides. The N-terminal and side chains may be modified by PEGylation, acetylation, formylation, addition of a fatty acid, addition of benzoyl, addition of bromoacetyl, addition of pyroglutamyl, succinylation, addition of tetrabutyoxycarbonyl and addition of 3-mercaptopropyl, acylations, biotinylation, phosphorylation, sulfation, glycosylation, introduction of maleimido group, chelating moieties, chromophores and fluorophores. In some embodiments, the peptide is attached or linked or conjugated to a second moiety (e.g., a heterologous moiety, a conjugate moiety). The heterologous moiety any molecule (chemical or biochemical, naturally-occurring or synthetic) which is different from the peptide. Exemplary heterologous moieties include, but are not limited to, a polymer, a carbohydrate, a lipid, a nucleic acid, an oligonucleotide, a DNA or RNA, an amino acid, peptide, polypeptide, protein, therapeutic agent, (e.g., a cytotoxic agent, cytokine), or a diagnostic agent.

For example, the C-terminus may be modified with amidation, addition of peptide alcohols and aldehydes, addition of esters, addition of p-nitoraline and thioesters and multipelantigens peptides. The N-terminal and side chains may be modified by PEGylation, acetylation, formylation, addition of a fatty acid, addition of benzoyl, addition of bromoacetyl, addition of pyroglutamyl, succinylation, addition of tetrabutyoxycarbonyl and addition of 3-mercaptopropyl, acylations (e.g. lipopeptides), biotinylation, phosphorylation, sulfation, glycosylation, introduction of maleimido group, chelating moieties, chromophores and fluorophores.

By way of further illustration, the method can comprise combining by vortex mixing (a) an organic phase comprising, consisting essentially of, or consisting of an organic solvent (e.g., methanol or ethanol) and an amphiphilic peptide as described herein (e.g., an M3mP6 peptide) with (b) an aqueous phase comprising, consisting essentially of, or consisting of a hydrophilic solvent (e.g., water), wherein the organic phase and aqueous phase do not comprise any lipid other than a lipid that might be covelantly attached to the amphiphilic peptide (see FIG. 3B).

The method of preparing peptide nanoparticles can provide nanoparticles of any suitable size. In some embodiments, the peptide nanoparticles provided by the method described herein have an average particle size (by volume) of about 5 to about 40 nm (e.g., about 5-30 nm, about 5-25 nm, about 5-15 nm, about 8-30 nm, about 8-25 nm, about 8-15 nm, about 10-30 nm, about 10-25 nm, about 10-15 nm, about 15-30 nm, about 15-25 nm, or about 15-25 nm), as determined by dynamic light scattering (DLS). In some embodiments, the high loading peptide nanoparticles have a particle size distribution such that about 95% or more of the particles (e.g., about 98% or more, or even about 99% or more) by volume have a particle size of about 6-25 nm as determined by DLS. The size of the nanoparticles can be controlled by changing in formulation, solvent and vortex-mixing conditions.

The peptide nanoparticles prepared by the provided method can further comprise other components, and the method can further comprising adding such components to the peptide nanoparticles or composition comprising the peptide nanoparticles. For instance, the aqueous phase used in the method can further comprise aqueous solutes, such as water-soluble peptides. Other components typically used in liposomes or micelles for drug delivery may also be used. In some embodiments, the method comprises the use of an organic phase consisting essentially of or consisting of (a) a hydrophobic or amphiphilic peptide or peptide conjugate, (b) one or more lipids that are free of a water-soluble polymer, (c) one or more lipids covalently attached to a water-soluble polymer, and (d) organic solvent, and/or the use of an aqueous phase consisting essentially of or consisting of a hydrophilic solvent, wherein "consisting essentially of" means that the organic or aqueous phase, respectfully, does not contain other components that would prevent the formation of a high loading peptide nanoparticle or render the high loading nanoparticle unsuitable for use to deliver a peptide in vivo.

The method of making peptide nanoparticles can further comprise drying the peptide nanoparticles after vortex mixing to produce a powder composition comprising the high loading peptide nanoparticle. Drying can be performed by any method, such as by lyophilization or spray drying. When the method comprises drying the peptide nanoparticle after vortex mixing, it is sometimes desirable to include a protectant (lyoprotectant or spray drying protectant) in the composition prior to drying. Protectants are known in the art (e.g., trehalose, leucine, or combination thereof) and can be incorporated before or after vortex mixing.

The peptide nanoparticles made according to the method provided herein can be used for any purpose, but are believed to be particularly well suited for diagnostic and therapeutic applications. In embodiments in which the peptide nanoparticle formed using the vortex mixing method described herein comprises FEEERA (SEQ ID NO: 6), FEEERL (SEQ ID NO: 8), or FEKEKL (SEQ ID NO: 10) that is lipidated (conjugated to a fatty acid, e.g., myr-FEEERA (SEQ ID NO: 6), myr-FEEERL (SEQ ID NO: 8), or myr-FEKEKL (SEQ ID NO: 10)), the peptide nanoparticle (particularly a high-loading peptide nanoparticle) produced according to the method provided herein can be used to treat ischemic disease, such as stroke and heart attack by administering to the subject in need of treatment the high-loading peptide nanoparticle.

In other embodiments, the peptide nanoparticles (particularly a high-loading peptide nanoparticle) produced according to the method provided herein may be used for inhibiting leukocyte function, such as leukocyte adhesion, spreading, migration, or chemotaxis, or for treating inflammation associated therewith, which method comprises of the step of contacting a leukocyte with the high loading peptide nanoparticle in an amount effective to inhibit leukocyte adhesion, spreading, migration, or chemotaxis, or inflammation associated therewith. Contacting the leukocyte with the peptide nanoparticle can be accomplished by administering the high loading peptide nanoparticle to a subject comprising the leukocyte.

In still other embodiments, the peptide nanoparticles (particularly a high-loading peptide nanoparticle) produced according to the method provided herein may be used for treating sepsis (a systemic inflammatory state caused by entry of microorganisms or their toxins into circulation), which method comprises of the step of administering the peptide nanoparticle to a subject in need of treatment for sepsis in an amount effective to treat the sepsis (e.g., reducing any symptom associated therewith).

The peptide nanoparticle prepared by the provided method can be administered to the subject by any suitable route of administration, such as systemically, e.g., parenterally (e.g., via intravenous, intramuscular or subcutaneous injection). The peptide nanoparticle prepared according to the disclosed method can be incorporated into a composition for use, which can comprise the nanoparticle composition and a suitable carrier, and may also contain adjuvants such as preservative, wetting agents, emulsifying agents and dispersing agents, isotonic agents and the like. In some embodiments, the peptide concentration incorporated in the nanoparticle composition is 1 mM or more, 5 mM or more, 10 mM or more, or even more than 10 mM (e.g., about 1-15 mM, about 5-15 mM, about 1-10 mM, or about 5-10 mM), enabling bolus injection in human subjects.

The following examples further illustrate the invention but, of course, should not be construed as in any way limiting its scope.

Example 1

This example demonstrates the preparation of high loading peptide nanoparticles (HPLN) comprising a lipidated peptide.

High loading peptide nanoparticles comprising M3mP6 (Myr-FEEERL (SEQ ID NO: 8)) or MB2mP6 (a myristoylated peptide derived from the Gα13 binding motif of β2 integrins) were produced using vortex-mixing (e.g., FIGS. 2A-2C) followed by lyophilization. The myristoylated peptide (60% mol/mol), PEG2000-DSPE (30% mol/mol), and L-α-phosphatidylcholine (10% mol/mol) were solubilized and mixed in 30% methanol/70% ethanol. The mixture is used as organic phase and drawn into a syringe. Separately, water is drawn into different syringe(s) as aqueous phase. The organic phase and water were then simultaneously injected into separate ports into a multiple inlet vortex mixer similar to that illustrated in FIGS. 2A-2C using a syringe pump at 1:12 ratio, and the mixed product directed into a flask. Lyophilization protectants (leucine/trehalos) were added to the product prior to lyophilization into powder.

Additional M3mP6 peptide nanoparticles were prepared with PEG2000-DSPE and phosphatidylcholine (PC) at different ratios as illustrated in FIGS. 3A-3C and FIG. 4. The ratios of M3mP6 peptide, PC, and PEG2000-DSPE greatly affect nanoparticle shape (FIGS. 3A-C) and size (FIG. 4).

The M3mP6 HLPN thus generated achieves a high M3mP6 peptide loading reaching >80% of total nanoparticle (mol/mol) (when such percentage of peptide was incorporated into during the process) and a high peptide concentration of >10 mM in injectable suspension. As analyzed by dynamic light scattering (DLS), the vast majority (99.8-100%) of these lipid-stabilized, PEG-coated M3mP6 HLPN have a particle size ranging between 6 nm to 25 nm (in different preparations) with occasional appearance of very small populations (0-0.2%) with larger diameters (~50-500 nm) (FIGS. 5A-5F). The lyophilized powder of M3mP6 is readily dissolvable in physiological saline for I.V. injection, and is stable for more than 18 months with the similar DLS profile and pharmacological effect when stored at −20° C., and for at least 2 weeks at room temperature (22° C.) (FIGS. 5A-5F).

Acute MTD (maximal tolerated dose) studies in rats revealed MTD exceeds 100 mg peptide bolus (80×converted efficacy dose), and rats exhibited no observable toxic reaction to M3mP6 HLPN (generated by vortex-mixing-lyophilization technique) after 5-day continuous infusion at 150 mg/kg/day. M3mP6 HLPN potently inhibited human platelet granule secretion and secretion-dependent secondary platelet aggregation induced by low dose thrombin in vitro (FIGS. 6A, 6B and 6C), but had no effect on platelet aggregation induced by high doses of thrombin (FIG. 6B), although platelet granule secretion was still partially inhibited by M3mP6 even at higher thrombin concentrations (FIG. 6C).

Figure 6:
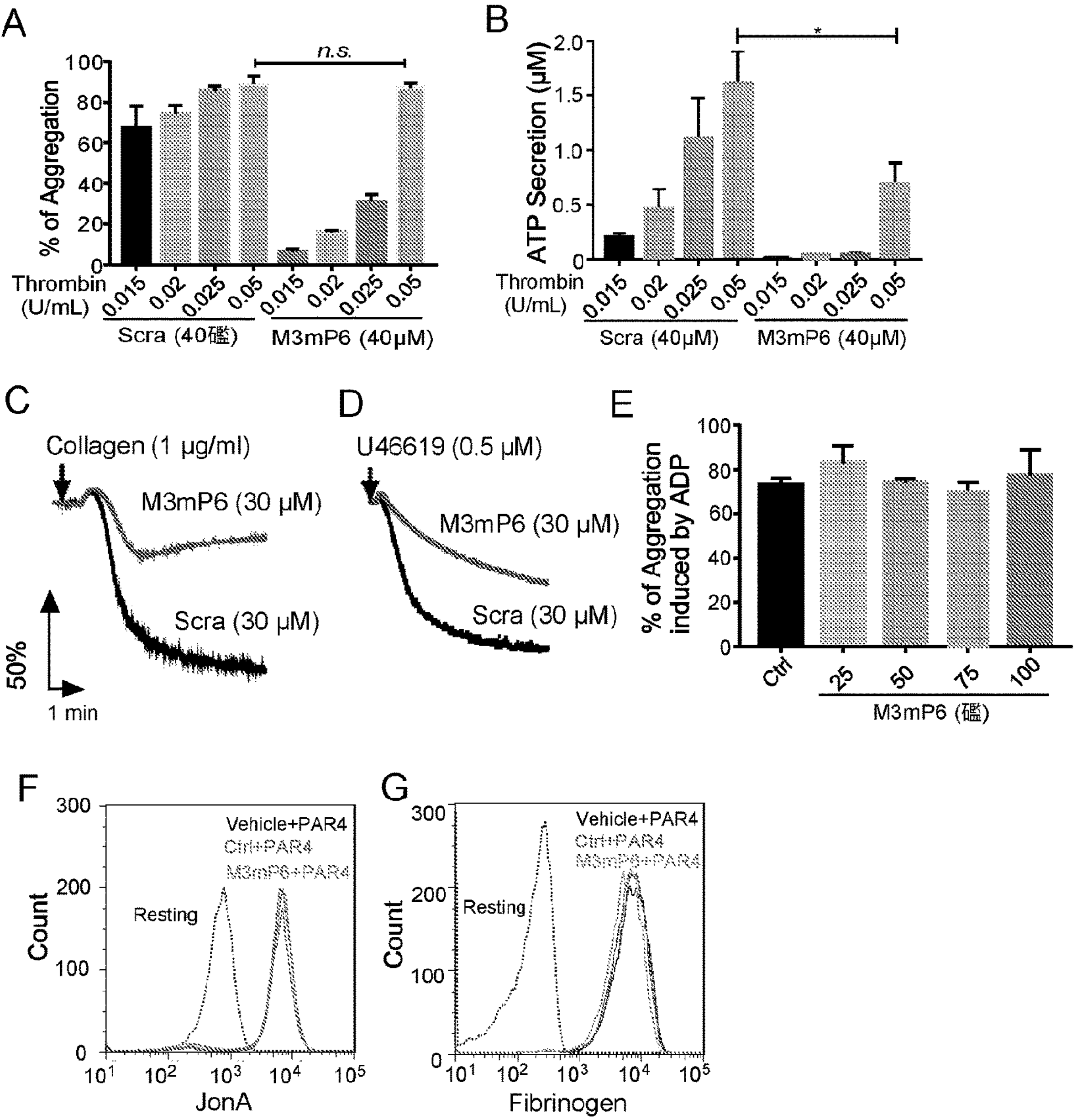

M3mP6 HLPN generated with vortex-mixing-lyophilization also partially inhibited thrombin (FIG. 6A), collagen (FIG. 6C) and U46619 (thromboxane A2 analog) (FIG. 6D) induced platelet aggregation and secretion (FIG. 4B) but did not affect ADP-induced platelet aggregation (FIG. 6E), nor JonA or fibrinogen binding to platelets induced by PAR4 agonist peptide FIG. 6F, 6G). These data confirm that M3mP6 prepared according to the method described herein does not affect inside-out signaling nor the ligand binding function of $\alpha_{IIb}\beta$, but inhibits secondary platelet responses to integrin outside-in signaling.

Figure 7:
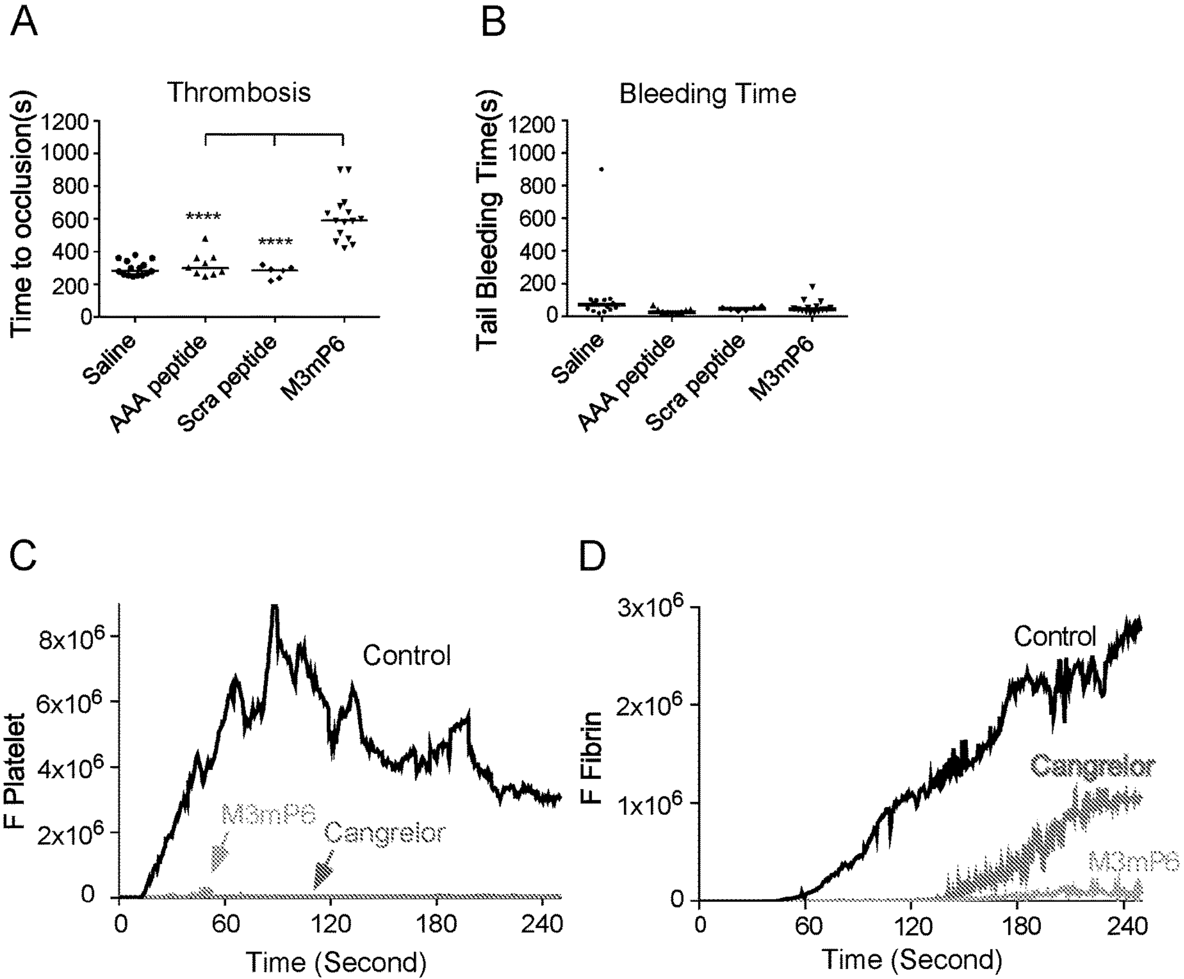

Pharmacokinetic studies indicated that blood and plasma levels of M3mP6 during rat 5-day infusion study showed a $t_{1/2-\lambda z}$ (half-life after cessation of infusion) of 3.1 (male) and 3.7 (female) hour (See Table 1 for PK characteristics). Consistently, anti-thrombotic efficacy was observed 5 minutes after injection, and lasted until after ~45 min. Thus, M3mP6 HLPN produced using vortex-mixing-lyophilization technique is a fast-acting and reversible anti-platelet drug suitable for i.v. injection, and if needed, its therapeutic effect can be prolonged with continuous infusion. Importantly, the same concentrations of M3mP6 HLPN that are highly efficacious in inhibiting occlusive thrombosis showed no effect on tail bleeding time in mice (FIG. 7A, 7B). Furthermore, M3mP6 HLPN did not cause prolonged bleeding in dog Buccal Mucosal Bleeding Time (BMBT) test (n=3 for each group, no statistical differences). These data suggest that M3mP6 HLPN generated using the methods described herein is a potent anti-thrombotic with minimal bleeding risk as tested both in rodents and dogs.

TABLE 1

Mean M3mP6 Peptide Pharmacokinetic Parameters

| | Dose: 25 mg/kg IVB/150 mg/kg/day IVI for 5 days | |
|---|---|---|
| Parameter | Female | Male |
| $C_{max}$ (ng/ml) | 193171 (23543)* | 264984 (NA) |
| $T_{max}$ (h) | 0.08 | 0.08 |
| $C_{ss}$ (ng/ml) | 131117 | 77621 |
| $AUC_{0\text{-}last\ (h\text{-}ng/ml)}$ | 17611767 (2160634)* | 9490148 (NA) |
| $AUC_{0\text{-}\infty\ (h\text{-}ng/ml)}$ | 17641938 | 9485816 |
| $\lambda_z$ ($h^{-1}$) | 0.223 | 0.177 |
| $t_{1/2\text{-}\lambda z}$ (h) | 3.1 | 3.9 |
| CL (ml/min/kg) | | |
| $CL_{AUC}$ | 0.7 | 1.4 |
| $CL_{css}$ | 0.8 | 1.3 |
| $V_{\lambda z}$ (l/kg) | 0.20 | 0.46 |

(*standard error; NA—standard error not able to be calculated due to sample sizes $<3$; IVB—intravenous bolus, IVI—intravenous infusion, $C_{max}$—maximum plasma concentration, $T_{max}$—time of Cmax, $C_{ss}$—steady-state plasma concentration during the continuous IV infusion, $AUC_{0\text{-}last}$—area under the plasma concetration-time curve from time zero (administration of IV bolus) to last plasma concentration (48 h after stopping infusion), $AUC_{0\text{-}\infty}$—AUC from time zero to infinity, $\lambda_z$—terminal elimination rate constant, $t_{1/2\text{-}\lambda z}$—terminal elimination half-life, $CL_{AUC}$—clearance estimated from the $AUC_{0\text{-}\infty}$, $CL_{css}$—clearance estimated from $C_{ss}$, $V_{\lambda z}$—distribution volume.)

Example 2

This example illustrates the comparative effect of M3mP6 HLPN (prepared substantially as described in Example 1) and cangrelor on intracvascular coagulation using laser-induced cremaster arteriolar thrombosis model in mice.

It was recently shown that outside-in signaling plays an important role in not only platelet thrombus formation but also intravascular coagulation under flow shear, an important aspect of thrombosis. This result is in contrast to the previous reports demonstrating the lack of effect of current anti-platelet drugs on intravascular coagulation. Thus, we tested the effect of M3mP6 HLPN generated by vortex-mixing-lyophilization on platelet thrombus formation and intravascular coagulation in comparison with cangrelor using the laser-induced cremaster arterial thrombosis model.

Whereas the two drugs have similarly potent effects in inhibiting platelet thrombus formation (FIG. 7C), M3mP6 HLPN almost completely inhibited intravascular fibrin clot formation at the site of vascular injury, whereas cangrelor only has moderate effect (FIG. 7D). Thus, M3mP6 HLPN is not only effective in inhibiting thrombus formation but also in inhibiting intravascular coagulation in vivo, and this effect is significantly superior than the most potent P2Y12 inhibitor cangrelor.

Example 3

This example illustrates the treatment of myocardial infarction-reperfusion (MI/R) injury with M3mP6 HLPN (prepared substantially as described in Example 1).

The current prevailing treatment for myocardial infarction/ischemia (MI) is to perform surgical or percutaneous coronary interventions to physically reopen the occluded artery. Reperfusion of ischemic tissues however, may cause myocardial ischemia/reperfusion (MI/R) injury, where an acute thrombo-inflammatory reaction of the ischemically injured tissues occurs upon re-exposure to oxygenated blood, resulting in damage to cardiac function and death. To evaluate the therapeutic effect of M3mP6 HLPN in treating MI and MI/R injury under conditions mimicking the clinical process of MI, severe mouse MI was induced by ligating the left anterior descending branch (LAD) of the coronary artery for 45 minutes before reopening to allow reperfusion. To mimic clinical treatment, M3mP6 or control HLPN were post-ischemically injected 10 minutes prior to reperfusion (FIG. 8A).

Figure 8:
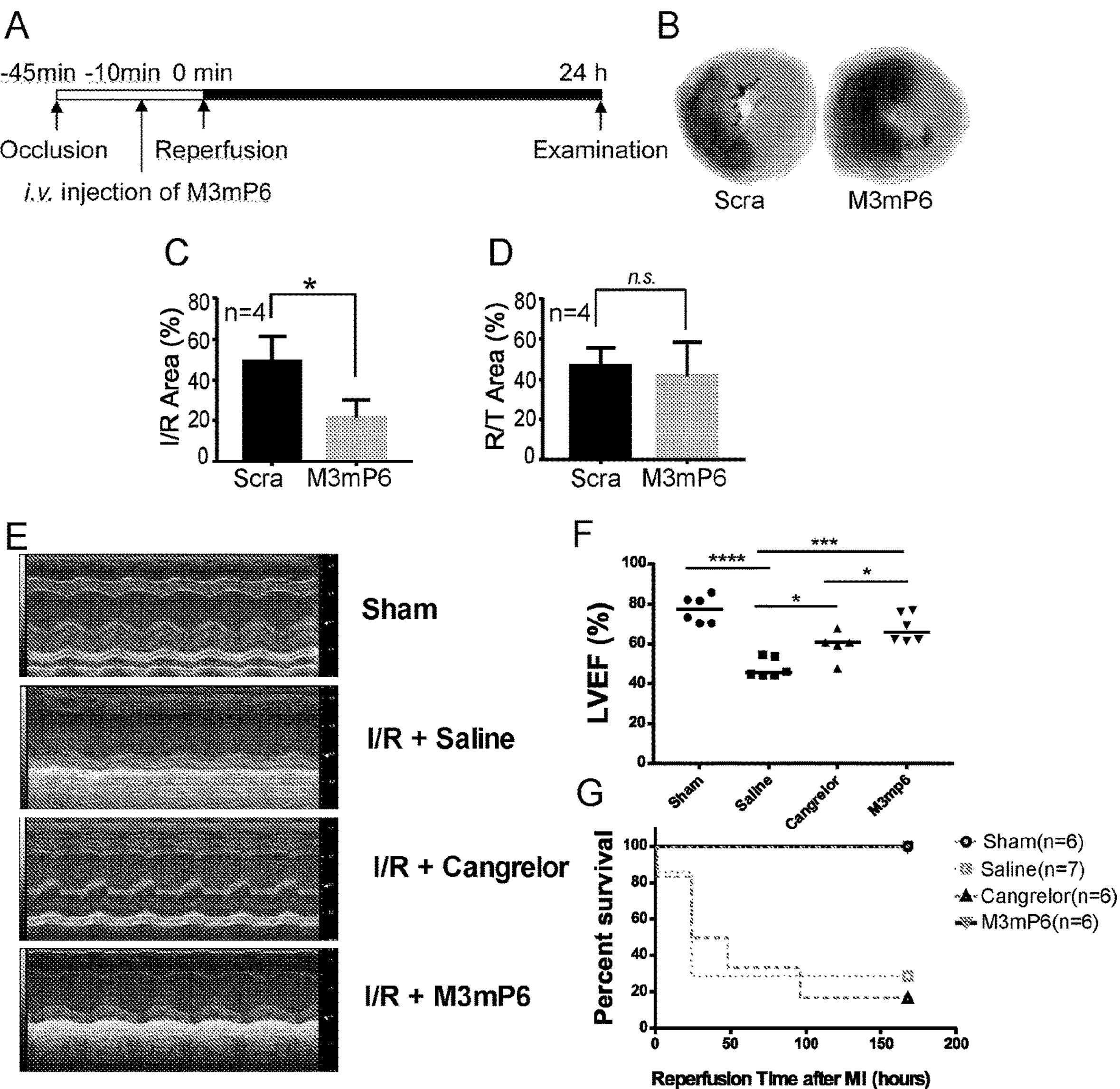

Compared with the control group, the M3mP6 HLPN treatment group showed significantly lower infarct area/risk area ration as indicated by triphenyltetrazolium chloride (TTC)/Evans Blue staining (FIGS. 8B-D), and prevented damage of cardiac function as indicated by echo cardiography performed at 24 hours after the procedure (FIGS. 8E and 8F). Importantly, M3mP6 greatly reduced mortality rate during the 7-day post-procedure monitoring (FIG. 8G). These data indicate that M3mP6 is an effective treatment of Ma-induced thrombosis/inflammation and cardiac injury in the mouse model.

Example 4

This example illustrates the generation of MB2mP6 HLPN and its effects on leukocyte function and systemic inflammation.

We also demonstrate that vortex-mixing-lyophilization technique can be used not only in generating M3mP6 HLPN, but also can be used for other peptides. Thus, we have generated HLPN of MB2mP6, a myristoylated peptide derived from the $G\alpha13$ binding motif of $\beta2$ integrins, by a vortex-mixing-lyophilization method substantially as described with respect to M3mP6 in Example 1. The MB2mP6 HLPN particles were found to inhibit inflammatory function of leukocytes and to be effective in treating sepsis in mice using the standard cecal ligation puncture (CLP) model.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of producing high-loading peptide nanoparticles comprising vortex-mixing (a) a hydrophobic or amphiphilic peptide or peptide conjugate, (b) one or more lipids that are free of a water-soluble polymer, (c) one or more lipids covalently attached to a water-soluble polymer, and (d) a hydrophilic solvent, to provide high-loading peptide nanoparticles.

2. The method of claim 1, wherein the peptide nanoparticles comprise greater than about 30 mole % of the hydrophobic or amphiphilic peptide or peptide conjugate.

3. The method of claim 1, wherein the high-loading peptide nanoparticles comprise about 2 to about 20 mole % of the one or more lipids free of a water-soluble polymer.

4. The method of claim 1, wherein the high-loading peptide nanoparticles nanoparticles comprise about 10 to about 60 mole % of the one or more lipids covalently attached to a water-soluble polymer.

5. The method claim 1, wherein the hydrophobic or amphiphilic peptide or peptide conjugate is a peptide conjugated to a hydrophobic molecule or a lipidated peptide.

6. The method of claim 1, wherein the one or more lipids covalently attached to a water-soluble polymer comprise a lipid conjugated to a polyoxyethylene polymer.

7. The method of claim 1, wherein the vortex mixing comprises combining in a vortex mixer (a) an organic phase comprising (i) the hydrophobic or amphiphilic peptide or peptide conjugate, (ii) one or more lipids that are free of a water-soluble polymer, (iii) the one or more lipids covalently attached to a water-soluble polymer, and (iv) an organic solvent; and (b) an aqueous phase comprising a hydrophilic solvent, optionally water.

8. The method of claim 1, wherein the vortex mixing comprises combining (a) a first stream of an organic phase comprising (i) the hydrophobic or amphiphilic peptide or peptide conjugate, (ii) one or more lipids that are free of a water-soluble polymer, (iii) the one or more lipids covalently attached to a water-soluble polymer, and (iv) an organic solvent; and (b) a second stream of an aqueous phase comprising a hydrophilic solvent, optionally, water; wherein the first and second streams are combined under conditions sufficient to create a vortex.

9. The method of claim 7, wherein the organic solvent comprises an alcohol.

10. The method of claim 7, wherein the organic phase and aqueous phase are combined at a ratio of 1:5 to 1:50 in the vortex mixer.

11. The method of claim 1, wherein the vortex mixing is performed in a multiple-inlet vortex mixer.

12. The method of claim 1, wherein the method further comprises drying the peptide nanoparticles to provide a powder composition comprising the peptide nanoparticles.

13. The method of claim 12, wherein drying the peptide nanoparticles comprises lyophilization or spray drying.

14. The method of claim 12, wherein the method comprises adding a drying protectant prior to drying the nanoparticles.

15. The method of claim 14, wherein the protectant comprises trehalose, leucine, or combination thereof.

16. The method of claim 1, wherein the amphiphilic or hydrophobic peptide or peptide conjugate comprises FEEERI (SEQ ID NO: 1), FEKEKI (SEQ ID NO: 2), FEKERI (SEQ ID NO: 3), RGT (SEQ ID NO: 4), EEERA (SEQ ID NO: 5), FEEERA (SEQ ID NO: 6), FEEERM (SEQ ID NO: 7), FEEERL (SEQ ID NO: 8), FEKEKM (SEQ ID NO: 9), FEKEKL (SEQ ID NO: 10), FEKERM (SEQ ID NO: 11), FEKERL (SEQ ID NO: 12), CFEEERAC (SEQ ID NO: 13), FEEERAR (SEQ ID NO: 14), FEEERARA (SEQ ID NO: 15), SIRYSGHpSL (SEQ ID NO: 16), KFEEERARAKWDT (SEQ ID NO: 17), RCLLPA (SEQ ID NO: 18), or LLARRPTKGIHEY (SEQ ID NO: 19) optionally conjugated to a hydrophobic moiety.

17. The method of claim 1, wherein the amphiphilic or hydrophobic peptide or peptide conjugate comprises myr-FEEERL (SEQ ID NO: 8), myr-FEEERA (SEQ ID NO: 6), myr-FEKEKL (SEQ ID NO: 10), myr-FEEERM (SEQ ID NO: 7), myr-FEKERM (SEQ ID NO: 11), myr-FEKERL (SEQ ID NO: 12), myr-FEKERI (SEQ ID NO: 3), myr-CFEEERAC (SEQ ID NO: 13), and myr-SIRYSGH (p) SL.

18. The method of claim 1, wherein the vortex mixing comprises (a) providing an organic phase comprising about 30-80 mole % of the hydrophobic or amphiphilic peptide, about 2-20 mole % of one or more lipids free of a water soluble polymer, and about 10-60 mole % of one or more lipid attached to a water soluble polymer dissolved in an organic solvent, and (b) vortex-mixing the organic phase with an aqueous phase at about 5 to 50 times the volume of the organic phase.

19. A method of preparing a peptide nanoparticle, the method comprising vortex mixing (a) an organic phase comprising an organic solvent and an amphiphilic peptide with (b) an aqueous phase, wherein the organic phase and aqueous phase do not comprise any free lipids;

or comprising vortex-mixing (a) an organic phase comprising a hydrophobic or amphiphilic peptide or peptide conjugate and one of (i) one or more lipids that are free of a water-soluble polymer, or (ii) one or more lipids covalently attached to a water-soluble polymer, and (b) a hydrophilic solvent, to provide lipid-stabilized peptide nanoparticles, wherein the amphiphilic peptide or peptide conjugate comprises myr-FEEERL (SEQ ID NO: 8), myr-FEEERA (SEQ ID NO: 6), myr-FEKEKL (SEQ ID NO: 10), myr-FEEERM (SEQ ID NO: 7), myr-FEKERM (SEQ ID NO: 11), myr-FEKERL (SEQ ID NO: 12), myr-FEKERI (SEQ ID NO: 3), myr-CFEEERAC (SEQ ID NO: 13), and myr-SIRYSGH(p)SL.

* * * * *

SEQUENCE LISTING

```
<160> NUMBER OF SEQ ID NOS: 20

<210> SEQ ID NO 1
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 1

Phe Glu Glu Glu Arg Ile
1               5


<210> SEQ ID NO 2
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 2

Phe Glu Lys Glu Lys Ile
1               5


<210> SEQ ID NO 3
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 3

Phe Glu Lys Glu Arg Ile
1               5


<210> SEQ ID NO 4
<211> LENGTH: 3
<212> TYPE: PRT
<213> ORGANISM: Artificial Sequence
<220> FEATURE:
<223> OTHER INFORMATION: Synthetic Sequence

<400> SEQUENCE: 4

Arg Gly Thr
1
```

<210> SEQ ID NO 5
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 5

Glu Glu Glu Arg Ala
1 5

<210> SEQ ID NO 6
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 6

Phe Glu Glu Glu Arg Ala
1 5

<210> SEQ ID NO 7
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 7

Phe Glu Glu Glu Arg Met
1 5

<210> SEQ ID NO 8
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 8

Phe Glu Glu Glu Arg Leu
1 5

<210> SEQ ID NO 9
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 9

Phe Glu Lys Glu Lys Met
1 5

<210> SEQ ID NO 10
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 10

Phe Glu Lys Glu Lys Leu
1 5

<210> SEQ ID NO 11

```
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 11

Phe Glu Lys Glu Arg Met
1               5


<210> SEQ ID NO 12
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 12

Phe Glu Lys Glu Arg Leu
1               5


<210> SEQ ID NO 13
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 13

Cys Phe Glu Glu Glu Arg Ala Cys
1               5


<210> SEQ ID NO 14
<211> LENGTH: 7
<212> TYPE: PRT
<213> ORGANISM: Artificial Sequence
<220> FEATURE:
<223> OTHER INFORMATION: Synthetic sequence

<400> SEQUENCE: 14

Phe Glu Glu Glu Arg Ala Arg
1               5


<210> SEQ ID NO 15
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 15

Phe Glu Glu Glu Arg Ala Arg Ala
1               5


<210> SEQ ID NO 16
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 16

Ser Ile Arg Tyr Ser Gly His Ser Leu
1               5


<210> SEQ ID NO 17
<211> LENGTH: 13
```

-continued

```
<212> TYPE: PRT
<213> ORGANISM: Artificial Sequence
<220> FEATURE:
<223> OTHER INFORMATION: Synthetic Sequence

<400> SEQUENCE: 17

Lys Phe Glu Glu Glu Arg Ala Arg Ala Lys Trp Asp Thr
1               5                   10


<210> SEQ ID NO 18
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 18

Arg Cys Leu Leu Pro Ala
1               5


<210> SEQ ID NO 19
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 19

Leu Leu Ala Arg Arg Pro Thr Lys Gly Ile His Glu Tyr
1               5                   10


<210> SEQ ID NO 20
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 20

Phe Ala Ala Ala Arg Leu
1               5
```